Dec. 2, 1975 L. H. SHOESMITH Plant Pat. 3,813
CHRYSANTHEMUM PLANT
(SPIRIT)
Filed Nov. 4, 1974
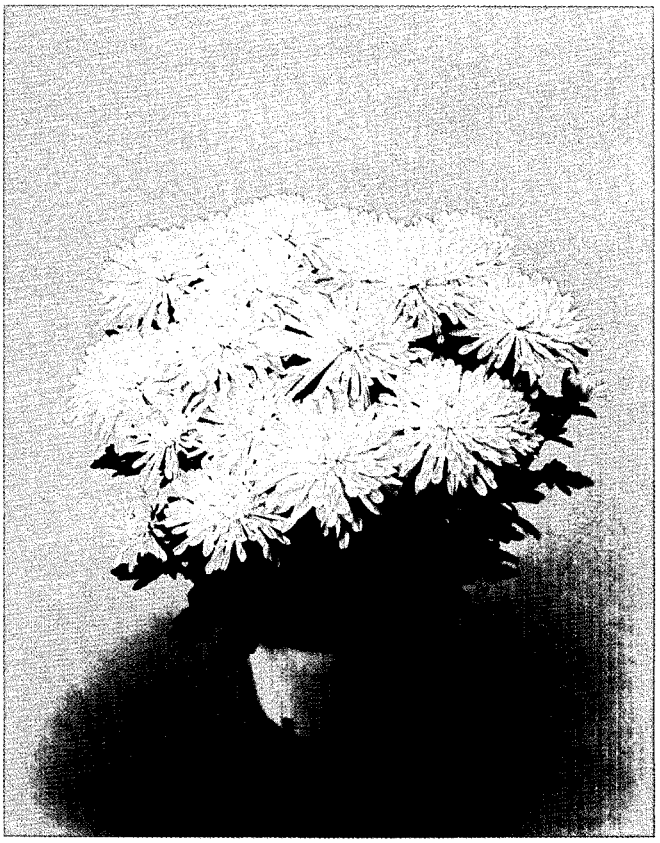
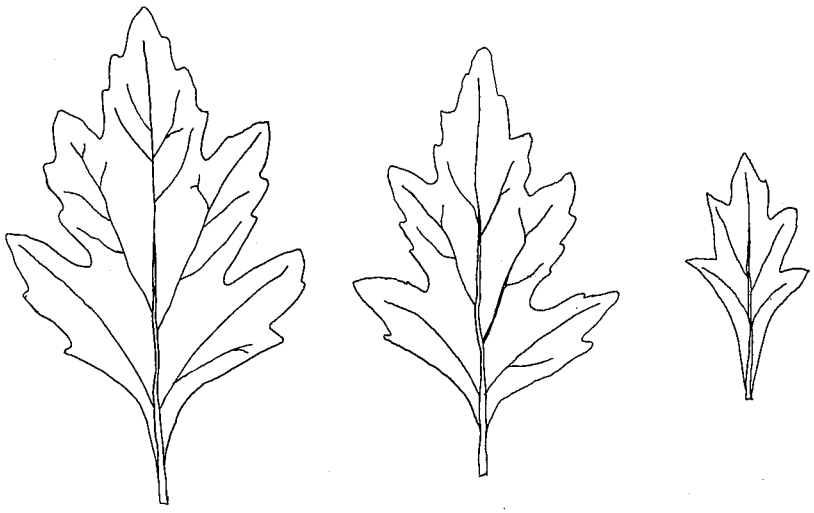

United States Patent

Plant Pat. 3,813
Patented Dec. 2, 1975

3,813

CHRYSANTHEMUM PLANT (SPIRIT)

Leonard H. Shoesmith, Westfield, Woking, Surrey, England, assignor to Pan-American Plant Company, West Chicago, Ill.

Filed Nov. 4, 1974, Ser. No. 520,428
Int. Cl. A01h *5/00*
U.S. Cl. Plt.—77 1 Claim

ABSTRACT OF THE DISCLOSURE

A new variety of chrysanthemum plant of the greenhouse pot plant type characterized by the pure white florets of its large, semi-incurve, decorative form of flower, its vigorous growth habit, and its year around ability to flower with a nine week response under photoperiod control.

BACKGROUND OF THE NEW PLANT

This new variety of chrysanthemum plant was discovered by me among a group of seedlings of unidentified parentage growing under glass at West Chicago, Ill., where I have carried on breeding efforts for many years to develop new and commercially advantageous chrysanthemum varieties. This plant was selected for propagation and test because of its pure white flower form and its vigorous growth habit and asexual propagation under my direction at West Chicago, Ill., by cuttings from the original plant and further reproduction through many generations at West Chicago, Ill., and Cortez, Fla., has demonstrated that the novel characteristics of the new plant hold true from generation to generation and appear to be firmly fixed.

DESCRIPTION OF THE DRAWING

My new variety of chrysanthemum plant is illustrated by the accompanying full color photographic drawing which shows the flower form and color characteristics of the plant; and which shows, by pen and ink drawings, the distinctive configuration of leaves of the plant taken at several stages of maturity.

DESCRIPTION OF THE NEW PLANT

The following is a detailed description of my new chrysanthemum plant, all color designations stated being according to Robert F. Wilson's Horticultural Colour Chart issued by The Royal Horticultural Society of London, England, with collaboration by The British Colour Council.

*The plant*

Origin: Seedling found among random pollinated greenhouse plants.
Parentage: Unidentified.
Classification:

Botanic—*Chrysanthemum morifolium.*
Commercial—Greenhouse pot plant.

Form: Perennial herbaceous bush.
Height: 11¾ inches, average.
Growth: Terminal, vigorous and upright.
Branching: Normal, sturdy and strong.
Foliage: Abundant, 8 leaves per stem.

Leaf size: Mature—3¼ inches long x 2¼ inches wide. Younger leaves are smaller.
Leaf Shape: Lobed, with acute lobe ends.
Venation: Pinnately veined.
Color: Upper side—Parsley Green 00962.
Color: Under side—Spinach Green 0960/3.
side—Spinach Green 0960/3.

Surface texture: Canescent.
Petioles: About 1¼ inches long.

*The bud*

Form: Global.
Size: ¼ inch diameter, ⅛ inch in depth.
Opening rate: Slow.
Color: When phyllaries first divide—Sap Green 62/2.
When florets begin to unfurl—Uranium Green 63/2.
Phyllaries: Outside of receptacle bears many distinct involucral, spear-shaped, upstanding bracts.

Color: Inside—Spinach Green 0960/2. Outside—Spinach Green 0960.
Surface texture: Canescent.
Peduncle: Erect and strong.
Length: ¾ inch to 1 5/16 inches.
Surface texture: Canescent.

*The flower*

Flowering capability: This plant can be flowered as desired, the year around, with photoperiod control.

Response: 9 week.
Recommended flowering: March to November in Northern states, year around in South.
Natural season flowering: October 27 to November 5.
Blooms:
Flower type: Semi-incurve; decorative spoon.
Borne: Either singly when disbudded or in multiples of 6 or more when grown as a spray plant.
Size: Large. Diameter—3¾ to 4¾ inches. Depth—¾ inch.
Shape: Cup-shaped when bloom first opens, becoming flatter as bloom matures.
Florets: Many in number, mostly ray petals which are tubular (spooned).
Form: Linear with obtuse apex.
Color: Outer floret—white. Inside floret—white. Reverse side—white. Immature inner florets will be of yellow color at the base which will fade to white as blossom matures.
Texture: Soft.
Appearance: Smooth.
Discoloration: None.
Peduncle: Sturdy and upright.
Length: ¾ to 1 5/16 inches.
Color: Scheeles Green 860/1.
Persistence: Petals hang on and dry.
Fragrance: Slight.
Lasting quality: 3 weeks on plant. Not recommended as

*Reproductive organs*

Stamens: Arrangement—5 syngenesious stamens, connate by their anthers to form a cylinder about the style.
Filaments: ⅛ inch long.
Color: Light yellow.
Pollen: Color—yellow.
Pistils: Number—1 to each ray floret.
Style: About ¼ inch long.
Stigma: Color—Sap Green 62/2.
Ovaries: Inferior, bicarpellate.

This plant is particularly characterized by the pure white color of its decorative form and the fact that it can be flowered at substantially any time of the year. The fairly large size of the flowers, on a pinched and disbudded plant, and the production of 5 or 6 breaks, gives the plant a distinct commercial advantage. The vigor and plant growth of this new variety of chrysanthemum is similar to that of the cultivar Puritan and it performs as described or as a spray pot plant from March through November in the north 42° latitude.

I claim:

1. A new and distinct variety of chrysanthemum plant, substantially as herein shown and described, characterized by the pure white of its relatively large flowers of the decorative type, by the soft golden glow that appears from the base of the immature florets at and around the center of the bloom until the bloom reaches full maturity, and by its many tubular and spooned ray florets.

No references cited.

ROBERT E. BAGWILL, Primary Examiner